United States Patent
Ichikawa (10) Patent No.: US 11,576,814 B2
(45) Date of Patent: Feb. 14, 2023

(54) OPHTHALMIC INSTRUMENT

(71) Applicant: CHUKYO MEDICAL CO., INC., Nagoya (JP)

(72) Inventor: Kazuo Ichikawa, Nagoya (JP)

(73) Assignee: CHUKYO MEDICAL CO., INC., Nagoya (JP)

(*) Notice: Subject to any disclaimer, the term of this patent is extended or adjusted under 35 U.S.C. 154(b) by 64 days.

(21) Appl. No.: 17/125,412

(22) Filed: Dec. 17, 2020

(65) Prior Publication Data

US 2021/0205127 A1    Jul. 8, 2021

(30) Foreign Application Priority Data

Jan. 7, 2020 (JP) .............................. JP2020-000766

(51) Int. Cl.
*A61F 9/007* (2006.01)

(52) U.S. Cl.
CPC ................................... *A61F 9/007* (2013.01)

(58) Field of Classification Search
CPC .............. A61F 9/00745; A61F 9/00736; A61F 2250/0093; A61F 9/007; A61F 9/0017; A61B 2017/320084; A61B 17/3421; A61M 39/10; A61M 3/0279; A61M 2039/1033; A61M 39/08; A61M 2210/0612; A61L 31/022; A61L 31/04
See application file for complete search history.

(56) References Cited

U.S. PATENT DOCUMENTS 3,528,425 A * 9/1970 Banko .............. A61B 17/32002
606/169
4,169,984 A * 10/1979 Parisi ................... B23Q 1/0036
433/119

(Continued)

FOREIGN PATENT DOCUMENTS

JP     H8-275969 A     10/1996
JP     H11505159 A     5/1999

(Continued)

OTHER PUBLICATIONS

Office Action dated Feb. 26, 2020 for the Japanese Application 2020-000766, with English Translation, 10 pages.

(Continued)

*Primary Examiner* — Timothy J Neal
*Assistant Examiner* — Andrew P. Restaino
(74) *Attorney, Agent, or Firm* — Kenichiro Yoshida (57) ABSTRACT

Provided is an ophthalmic instrument that is for retaining a tube member for providing communication between the inside and the outside of an eyeball, such that the tube member is stuck into an outer membrane of the eyeball and that is suitable for retaining the tube member at an outer peripheral portion of a cornea. An ophthalmic instrument includes a main body and a needle portion connected to the main body. The main body has a straight portion and a bent portion. When attaching a tube member to an eyeball, first, the needle portion is inserted through the tube member, and the tube member is stuck into an outer peripheral portion of a cornea as the outer membrane of the eyeball while a hole is made in the outer peripheral portion of the cornea with the needle portion.

2 Claims, 7 Drawing Sheets

(56) References Cited

U.S. PATENT DOCUMENTS

| | | | | |
|---|---|---|---|---|
| 5,112,339 A | * | 5/1992 | Zelman | ............... A61F 9/00745 606/127 |
| 5,222,937 A | * | 6/1993 | Kagawa | ......... A61B 17/320068 606/169 |
| 5,653,724 A | * | 8/1997 | Imonti | ................ A61F 9/00745 606/107 |
| 5,792,099 A | | 8/1998 | DeCamp | |
| 5,993,409 A | * | 11/1999 | Maaskamp | ......... A61F 9/00745 604/27 |
| 2017/0189232 A1 | * | 7/2017 | Yan | ......................... A61L 31/04 |
| 2019/0388271 A1 | * | 12/2019 | Abt | ......................... A61B 3/13 |

FOREIGN PATENT DOCUMENTS

| | | |
|---|---|---|
| JP | 2019025023 A | 2/2019 |
| WO | 2019/026787 A1 | 2/2019 |

OTHER PUBLICATIONS

European Search Report dated Jun. 4, 2021 for corresponding EP application (EP20217629.3), 7 pages.

\* cited by examiner

OPHTHALMIC INSTRUMENT

RELATED APPLICATIONS

This application claims the priority of Japanese Patent Application No. 2020-000766 filed on Jan. 7, 2020, which is incorporated herein by reference.

BACKGROUND OF THE INVENTION

Field of the Invention

This disclosure relates to an instrument for retaining a tube member for providing communication between the inside and the outside of an eyeball, at the eyeball during ophthalmic surgery.

Description of Related Art

Hitherto, as an instrument for retaining (attaching) a tube member, used in ophthalmic surgery, at an eyeball, an instrument for making a hole in an eyeball with a needle portion in a state where the needle portion is inserted through a cannula as a tube member and retaining the cannula at the same time such that the cannula is stuck into the outer membrane of the eyeball, has been known (see, for example, Japanese Laid-Open Patent Publication No. 2019-25023).

Meanwhile, for example, in the case of retaining a tube member at a cornea, it is desirable to retain the tube member at an outer peripheral portion of the cornea as much as possible. This is because, if a hole is made near the center of the cornea, the shape of the cornea may be deformed, or the needle portion approaching the eyeball may be seen by the person to be operated, which may give fear to the person to be operated. In addition, in the case of retaining the tube member at the outer peripheral portion of the cornea, in order to prevent the iris or the crystalline lens from being damaged by the needle portion or the tube member, it is necessary to direct the tip end of the needle portion in a direction deviating from the iris and the crystalline lens. Specifically, when a front-rear direction is defined with the cornea apex side as a front side and the center side of the retina as a rear side, it is necessary to perform a manipulation of retaining the tube member at the eyeball in a state where the needle portion is inclined as much as possible in a lateral direction crossing the front-rear direction (more specifically, for example, the needle portion is directed slightly obliquely frontward).

However, for the conventional instruments disclosed in Japanese Laid-Open Patent Publication No. 2019-25023, etc., it is assumed that a hole is made toward the rear side (retina center side) with respect to the sclera on the outer side of the vitreous body located behind the iris and the crystalline lens, and a tube member is retained at the sclera. Thus, there is a problem that it is difficult to perform a manipulation of retaining the tube member at the outer peripheral portion of the cornea.

This disclosure has been made in view of the above-described problem, and an object of this disclosure is to provide an ophthalmic instrument suitable for retaining a tube member at an outer peripheral portion of a cornea.

SUMMARY OF THE INVENTION

In order to solve the aforementioned problem, the ophthalmic instrument of this disclosure is an instrument including:

a needle portion; and a main body having a straight portion extending in a straight manner, and connected at one end side thereof to the needle portion, wherein the instrument is for retaining a tube member for providing communication between the inside and the outside of an eyeball such that the tube member is stuck into an outer membrane of the eyeball, by holding the straight portion in a state where the needle portion is inserted through the tube member, sticking the tube member into the outer membrane while making a hole in the outer membrane of the eyeball with the needle portion, and then withdrawing the needle portion from the outer membrane, the tube member is a member to be attached to the outer membrane during ophthalmic surgery and is a member to be removed from the eyeball after the ophthalmic surgery, and the needle portion is provided at an angle with respect to the straight portion.

According to this, since the needle portion is provided at the angle with respect to the straight portion, for example, a space for the straight portion serving as a grip portion is easily ensured when retaining the tube member at an outer peripheral portion of a cornea in a direction deviating from an iris and a crystalline lens, so that it is easy to perform a manipulation of retaining the tube member at the outer peripheral portion of the cornea.

DESCRIPTION OF THE PREFERRED EMBODIMENTS

First Embodiment

Figure 1:
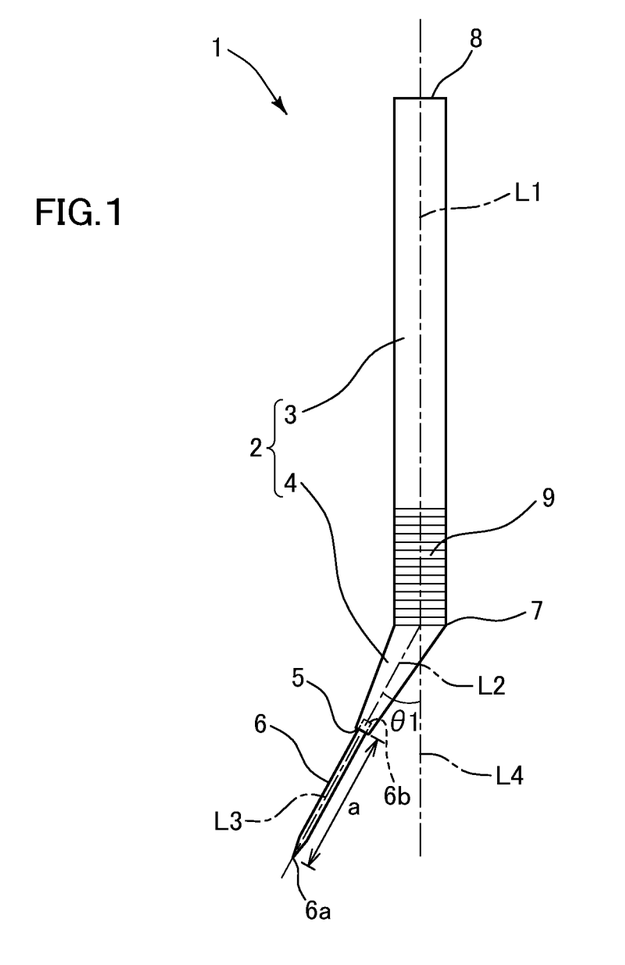
FIG. 1 is a side view of an ophthalmic instrument according to a first embodiment.

Hereinafter, a first embodiment of this disclosure will be described with reference to the drawings. An ophthalmic instrument 1 in FIG. 1 is a tube member retaining instrument for retaining a tube member 10 (see FIG. 2) such that the tube member 10 is stuck into the cornea of an eye (eyeball) to be operated, during ophthalmic surgery.

The instrument 1 includes a rod-shaped main body 2 (rod-shaped portion) and a needle portion 6 connected to one end portion in the longitudinal direction of the main body 2. The main body 2 is formed in a longitudinal shape in which one end side thereof in the longitudinal direction is bent. Specifically, the main body 2 has a straight portion 3 extending in a straight manner and a bent portion 4 continuous with one end 7 of the straight portion 3. The straight portion 3 and the bent portion 4 are formed, for example, as an integrally molded member made of the same material (for example, resin).

The straight portion 3 serves as a grip portion to be held by an operator (doctor), in other words, as a manipulation portion to be manipulated for retaining the tube member 10 at the cornea. In addition, the length along a central axis L1 of the straight portion 3 is, for example, larger than the length along a central axis L2 of the bent portion 4. Moreover, a cross-section, of the straight portion 3, perpendicular to the central axis L1 is, for example, circular. That is, the straight portion 3 is formed, for example, in a round bar shape or a columnar shape, but may be formed in another shape other than this shape. A portion 9, of the straight portion 3, at the end portion 7 side to which the bent portion 4 is connected is subjected to processing for making it difficult to cause slipping when the straight portion 3 is held with fingers (for example, formed with a rugged surface).

The bent portion 4 extends in a straight manner or in a curved manner in a direction different from the direction in which the central axis L1 of the straight portion 3 extends. That is, the bent portion 4 is provided at an angle with respect to the straight portion 3. The bent portion 4 serves as an angle imparting portion that imparts an angle to the needle portion 6 with respect to the straight portion 3. An angle θ1 formed between the central axis L2 of the bent portion 4 (in other words, the direction in which a tip end 5 of the bent portion 4 is directed) and an extension line L4 that is a straight line obtained by extending the central axis L1 of the straight portion 3 outwardly from the end portion 7 on the bent portion 4 side in the same direction as that of the axis L1, is set so as to be, for example, greater than 0 degrees and equal to or less than 90 degrees. More specifically, the angle θ1 is set to an angle that is equal to or greater than 20 degrees and equal to or less than 70 degrees (for example, 45 degrees). In other words, the angle θ1 is also an angle formed between a central axis L3 of the needle portion 6 and the extension line L4.

Moreover, the bent portion 4 is formed, for example, in a shape in which a cross-section thereof perpendicular to the central axis L2 is circular (that is, in a round bar shape or a columnar shape), and is also formed in a shape in which the diameter thereof gradually decreases from the portion 7 connected to the straight portion 3 toward the tip end 5 of the bent portion 4 (that is, in a tapered shape). The bent portion 4 does not have to be formed in a tapered shape. The tip end 5 of the bent portion 4 (main body 2) is directed in a direction determined by the angle θ1.

Figure 2:
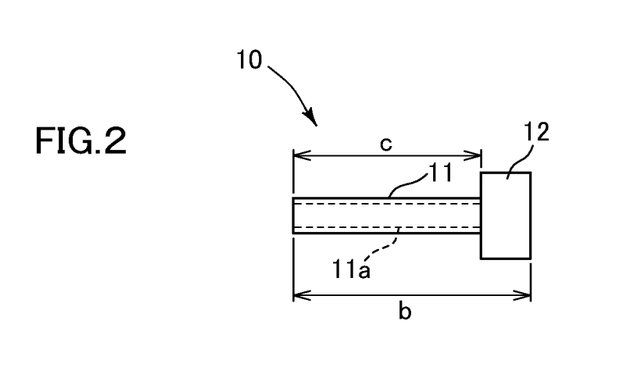
FIG. 2 is a side view of a tube member.

The tip end 5 of the bent portion 4 may be formed in a shape that allows the tube member 10 to be engaged when the tube member 10 in FIG. 2 is mounted on the instrument 1 (for example, a claw portion, a fitting recess portion, a fitting projection portion, or the like), or such a shape does not have to be formed.

Moreover, the length along the central axis L2 of the bent portion 4 is preferably smaller than the length along the central axis L1 of the straight portion 3, and can be, for example, equal to or less than 30% of the length of the straight portion 3. This is because, if the bent portion 4 is excessively long, the distance between the straight portion 3 serving as a grip portion and the needle portion 6 becomes large, resulting in a decrease in manipulability when manipulating the needle portion 6 while holding the straight portion 3.

The boundary portion 7 between the straight portion 3 and the bent portion 4 serves as a direction change portion that changes the direction in which the main body 2 extends, to another direction. The main body 2 has a single direction change portion 7.

The needle portion 6 extends in a straight manner. In other words, the needle portion 6 does not have a bent portion. A tip end 6a of the needle portion 6 is sharp. The needle portion 6 is made of metal, and is, for example, formed as a molded member separate from the main body 2 made of resin. The needle portion 6 is undetachably or detachably connected to the tip end 5 of the bent portion 4 such that the central axis L2 of the bent portion 4 and the central axis L3 of the needle portion 6 coincide with each other. The needle portion 6 is provided such that a portion 6b on the base end side of the needle portion 6 is embedded in the bent portion 4 and the tip end 6a side of the needle portion 6 is exposed. The entirety of the needle portion 6 is provided at the angle θ1 with respect to the straight portion 3.

Figure 3:
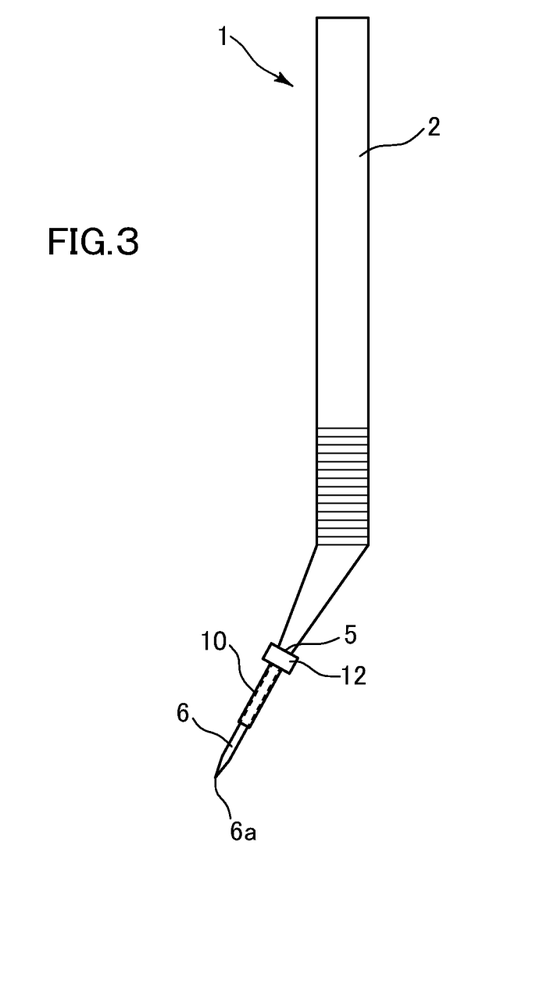
FIG. 3 is a diagram showing that the tube member is mounted on the ophthalmic instrument according to the first embodiment.

Moreover, a length a (see FIG. 1) of the needle portion 6 is larger than a length b of the tube member 10 in FIG. 2. That is, the length a of the needle portion 6 is set such that, as shown in FIG. 3, a portion, from the tip end 6a, of the needle portion 6 projects (penetrates) from an opening of the tube member 10 when the tube member 10 is mounted on the instrument 1 such that the needle portion 6 is inserted through the tube member 10. In addition, the length a of the needle portion 6 is set to a length that allows the needle portion 6 to break through the cornea and reach the interior of the anterior chamber on the inner side (region between the cornea and the iris) when the needle portion 6 is stuck into the cornea and that prevents the tip end 6a of the needle portion 6 having reached the interior of the anterior chamber from protruding from the interior of the anterior chamber. Specifically, the length a of the needle portion 6 is set so as to be, for example, equal to or greater than 3 mm and equal to or less than 10 mm.

The tube member 10 (cannula) in FIG. 2 is a member that is attached to the outer membrane (cornea or sclera) of an eyeball to provide communication between the inside and the outside of the eyeball, during ophthalmic surgery such as glaucoma surgery. Since the tube member 10 is a member temporarily attached to the eyeball during ophthalmic surgery, the tube member 10 is removed from the eyeball after the ophthalmic surgery. In addition, the tube member 10 may be a liquid injection tube through which a liquid is injected into the anterior chamber during surgery to keep the intraocular pressure constant and suppress outflow of blood into the eye, may be an instrument insertion tube through which a surgical instrument is inserted into the anterior chamber, or may be a light introduction tube through which light for making it easier to see the inside of the eye is introduced into the anterior chamber during surgery.

The tube member 10 has a main body tube 11 made of metal, and a large diameter portion 12 connected to one end of the main body tube 11. The main body tube 11 is a tube that extends in a straight manner and has a hole 11a formed therein so as to penetrate from one end to another end in the axial direction thereof. A length c (see FIG. 2) of a portion, of the main body tube 11, exposed from the large diameter portion 12 is set to a length that is larger than the thickness of the cornea and that prevents the tip end of the main body tube 11 from protruding from the interior of the anterior chamber in a state where the main body tube 11 is stuck into the cornea. Specifically, the length c is set so as to be, for example, equal to or greater than 2 mm and equal to or less than 10 mm. In addition, from the viewpoint of preventing the shape of the cornea from being deformed when the main body tube 11 is stuck into the cornea, or from the viewpoint of allowing a hole formed in the cornea to close naturally when the main body tube 11 is removed after surgery, the outer diameter of the main body tube 11 is preferably smaller, and can be, for example, equal to or less than 1 mm.

The large diameter portion 12 is, for example, made of metal and formed in a cylindrical shape having an outer diameter larger than the outer diameter of the main body tube 11. The large diameter portion 12 is a portion that serves as a stopper such that the entirety of the tube member 10 is not inserted into the eye. That is, when the tube member 10 is retained at the cornea, whereas the main body tube 11 is inserted into the anterior chamber, the large diameter portion 12 is exposed on the outer surface of the cornea. The large diameter portion 12 may have a backflow suppression function (check valve function) for suppressing the fluid in the eye from flowing out from the large diameter portion 12 via the main body tube 11.

Next, a procedure for retaining the tube member 10 at a cornea using the instrument 1 will be described with reference to FIG. 4 to FIG. 6. When retaining the tube member 10 at the cornea, the operator lays a person to be operated down and positions themselves around the face (on the ear side or head side) of the person to be operated. In addition, referring to FIG. 4, a portion at which the tube member 10 is retained is preferably an outer peripheral portion 21a of a cornea 21 (near the boundary between the cornea 21 and a sclera 25). This is because, when the tube member 10 is retained at the outer peripheral portion 21a of the cornea 21, deformation of the shape of the cornea 21 due to a hole being made in the cornea 21 by the needle portion 6 can be suppressed, and the needle portion 6 approaching an eye 20 can be inhibited from being seen by the person to be operated. In addition, the retaining portion 21a for the tube member 10 can be, for example, an ear-side portion of the outer peripheral portion of the cornea 21.

First, as shown in FIG. 3, the needle portion 6 is inserted through the tube member 10 to mount the tube member 10 onto the instrument 1. At this time, the end surface of the large diameter portion 12 of the tube member 10 is brought into contact with the tip end 5 of the main body 2, thereby protruding the portion, from the tip end 6a, of the needle portion 6 from the tube member 10 while holding the tube member 10 at the main body 2 or the needle portion 6.

Figure 4:
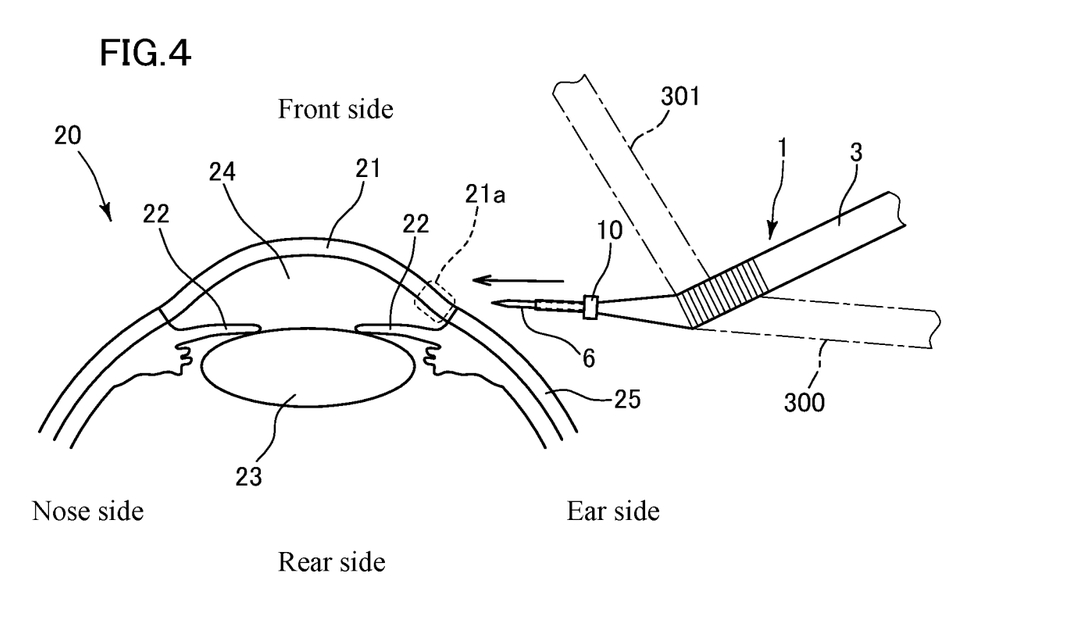
FIG. 4 illustrates a state where the ophthalmic instrument having the tube member mounted thereon is caused to approach an outer peripheral portion of a cornea in an anterior ocular segment shown by tomography, in order to retain the tube member at the outer peripheral portion of the cornea.
Figure 5:
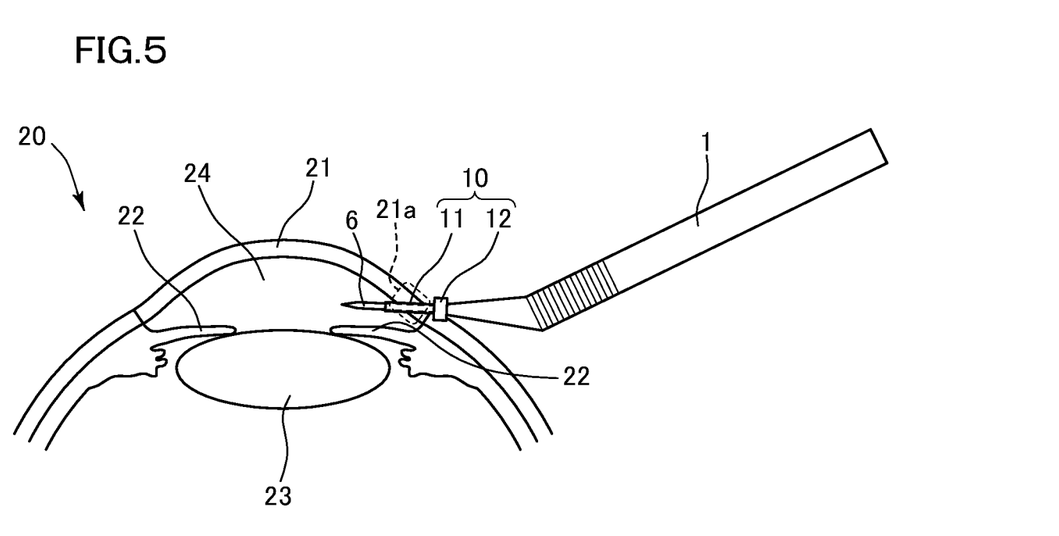
FIG. 5 is a diagram following FIG. 4 and illustrates a state where the needle portion is stuck into the outer peripheral portion of the cornea and the tube member is inserted into the outer peripheral portion of the cornea at the same time.
Figure 6:
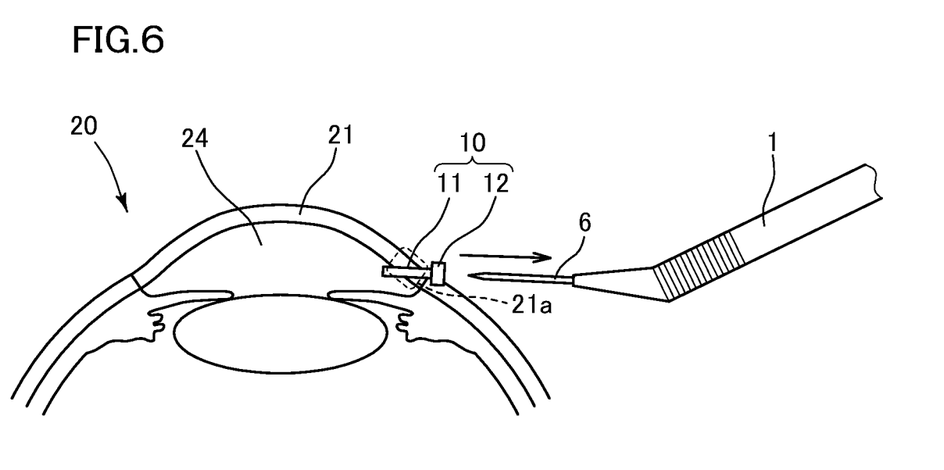
FIG. 6 is a diagram following FIG. 5 and illustrates a state where the ophthalmic instrument is pulled out after the tube member is inserted into the outer peripheral portion of the cornea.

Thereafter, the operator retains the tube member 10 at the outer peripheral portion 21a of the cornea 21 by performing manipulation while holding the straight portion 3 of the instrument 1 having the tube member 10 mounted thereon (see FIG. 4 to FIG. 6). At this time, for example, the operator holds the straight portion 3 so as to pinch the portion 9 (see FIG. 1) at the tip end side of the straight portion 3 with a plurality of fingers (in other words, like holding a pencil).

Specifically, first, the operator causes the entirety of the instrument 1 to approach the outer peripheral portion 21a in a state where the tip end of the needle portion 6 is directed toward the outer peripheral portion 21a of the cornea 21 (see FIG. 4). At this time, the needle portion 6 is preferably directed so as to be inclined as much as possible in the right-left direction in the sheet of FIG. 4 in order to prevent the needle portion 6 and the tube member 10 from coming into contact with an iris 22 or a crystalline lens 23 when the needle portion 6 is stuck into the cornea 21. More specifically, the needle portion 6, for example, is preferably directed slightly obliquely frontward (toward the cornea apex side).

Thereafter, the operator inserts the tube member 10 into the outer peripheral portion 21a while sticking the needle portion 6 into the outer peripheral portion 21a of the cornea 21 to make a hole therein (see FIG. 5). At this time, the operator performs a manipulation of inserting the tube member 10 until the large diameter portion 12 of the tube member 10 comes into contact with the outer surface of the outer peripheral portion 21a. In a state where the needle portion 6 is stuck, the tip end of the needle portion 6 and the tip end of the tube member 10 (main body tube 11) are located in an anterior chamber interior 24 so as not to be in contact with the iris 22 or the crystalline lens 23.

Thereafter, the operator withdraws the instrument 1 (needle portion 6) from the cornea 21, thereby retaining only the tube member 10 such that the tube member 10 is stuck into the cornea outer peripheral portion 21a (see FIG. 6). When withdrawing the instrument 1, the operator may hold the large diameter portion 12 of the tube member 10 with a pair of forceps or the like in order to prevent the tube member 10 from coming out of the cornea 21.

Figure 7:
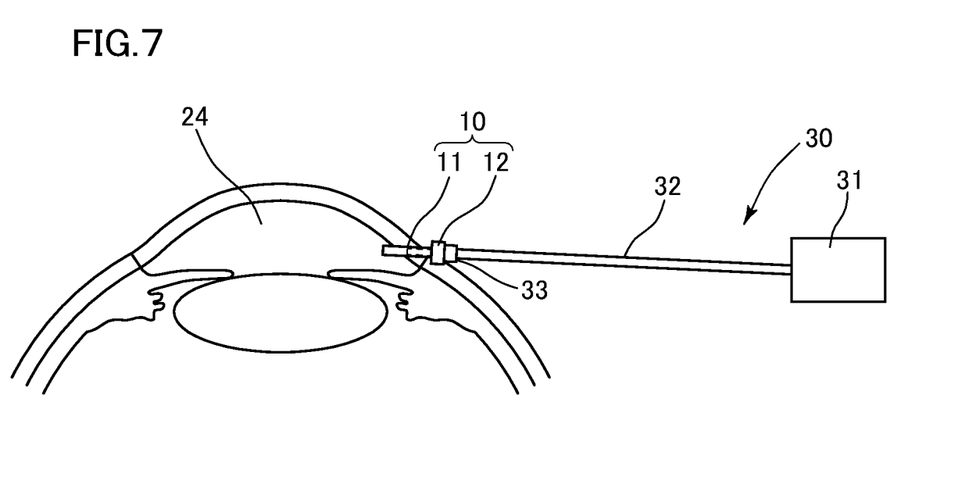
FIG. 7 is a diagram showing that a liquid injection device is connected to the tube member retained at the outer peripheral portion of the cornea.

Through the above procedure, the tube member 10 is retained so as to be stuck into the cornea outer peripheral portion 21a. During subsequent surgery, for example, in order to suppress outflow of blood into the eye, a liquid (water) is injected into the anterior chamber via the tube member 10 such that the pressure (intraocular pressure) in the anterior chamber is kept constant. In this case, as shown in FIG. 7, a liquid injection device 30 is connected to the tube member 10. The liquid injection device 30 has a control unit 31, an injection tube 32, and a tubular connector 33. One end of the injection tube 32 is connected to the control unit 31, and the other end of the injection tube 32 is connected to the connector 33. The injection tube 32 and the tube member 10 are connected to each other by inserting the connector 33 into a hole 11a of the tube member 10 from the large diameter portion 12 side. The control unit 31 has a function of monitoring the pressure in the anterior chamber (pressure when injecting the liquid into the anterior chamber), and the liquid is injected into the anterior chamber via the injection tube 32 and the tube member 10 connected to the injection tube 32, such that this pressure is kept constant.

As glaucoma surgery, for example, trabeculectomy for reducing the intraocular pressure abnormally increased by making the aqueous humor smoothly flow is performed. In this case, a cut for introducing a trabeculectomy instrument (cutter) into an anterior chamber interior 24 is formed in the cornea 21. This cut is formed in a portion different from the retaining portion 21a (see FIG. 4) for the tube member 10 for liquid injection. Outflow of the anterior chamber fluid through the cut can be suppressed by injecting a liquid into the anterior chamber interior 24 via the tube member 10 as appropriate to keep the pressure of the anterior chamber interior 24 high.

After the surgery, the tube member 10 is removed from the eyeball by holding and pulling out the large diameter portion 12 of the tube member 10 with a pair of forceps or the like. Thereafter, if necessary, suture is performed to close the hole formed in the cornea outer peripheral portion 21a.

As described above, in this embodiment, since the needle portion 6 is provided at an angle with respect to the straight portion 3 serving as a grip portion, it is easy to perform a manipulation of retaining the tube member 10 at the cornea outer peripheral portion 21a. That is, when a front-rear direction is defined with the cornea apex side as a front side and the center side of the retina (not shown) as a rear side in the sheets of FIG. 4 to FIG. 6, the straight portion 3 can be located on the front side (the face side of the operator) in the case of performing manipulation in a state where, at the cornea outer peripheral portion 21a, the needle portion 6 is inclined as much as possible in a lateral direction crossing the front-rear direction as shown in FIG. 4 to FIG. 6. Furthermore, by setting the angle θ1 (see FIG. 1) between the needle portion 6 and the straight portion 3 so as to be greater than 0 degrees and equal to or less than 90 degrees, it is possible to keep the straight portion 3 away from the eye 20 to be operated to the right side in the sheets of FIG. 4 to FIG. 6 when performing the manipulation shown in FIG. 4 to FIG. 6. Accordingly, the straight portion 3 can be kept away from the surface of the face of the person to be operated, so that a space for the straight portion 3 and the hand of the operator holding the straight portion 3 can be easily ensured. In addition, since the straight portion 3 is located on the front side near the face of the operator, it is easy to manipulate the straight portion 3.

Moreover, by setting the angle θ1 (see FIG. 1) so as to be greater than 0 degrees and equal to or less than 90 degrees, it becomes easy to perform a manipulation of causing the needle portion 6 to penetrate the cornea 21, as compared to the case where the angle θ1 is greater than 90 degrees (the case where the straight portion is located at the position of a broken line 301 in FIG. 4). That is, in the case where the straight portion 3 is located at the position of a solid line in FIG. 4 (the case where the angle θ1 in FIG. 1 is greater than 0 degrees and equal to or less than 90 degrees), the operator can manipulate the straight portion 3 while holding the straight portion 3 like holding a pencil, thus the manipulation is easy, and manipulation force applied to the straight portion 3 by the operator can be easily transmitted to the needle portion 6.

On the other hand, in the case where the needle portion and the straight portion are formed on the same straight line (the case where the straight portion is located at the position of a broken line 300 in FIG. 4), the straight portion 300 is located on the rear side (the side closer to the surface of the face of the person to be operated), and thus it is difficult to ensure a space for the straight portion 300 and the hand of the operator holding the straight portion 300. In addition, since the straight portion 300 is located on the side away from the face of the operator, it is difficult for the operator to manipulate the straight portion 300.

Moreover, in the case where the angle between the straight portion and the needle portion is greater than 90 degrees (the case where the straight portion is located at the position of the broken line 301 in FIG. 4), the straight portion 301 is closer to the eye 20 to be operated, so that the straight portion 301 or the hand of the operator holding the straight portion 301 makes it difficult for the operator to see the eye 20 to be operated.

In this embodiment, since the main body 2 is bent, and the needle portion 6 is not bent and is composed of only a straight portion, the configuration of the needle portion 6 can be simplified, and, for example, a conventional needle portion can be used.

Second Embodiment

Next, the second embodiment will be described focusing on the differences from the first embodiment. The tube member retaining instrument of the first embodiment is configured such that the main body is bent and the needle portion is not bent. However, a tube member retaining instrument of the second embodiment is configured such that the main body is not bent and the needle portion is bent.

Figure 8:
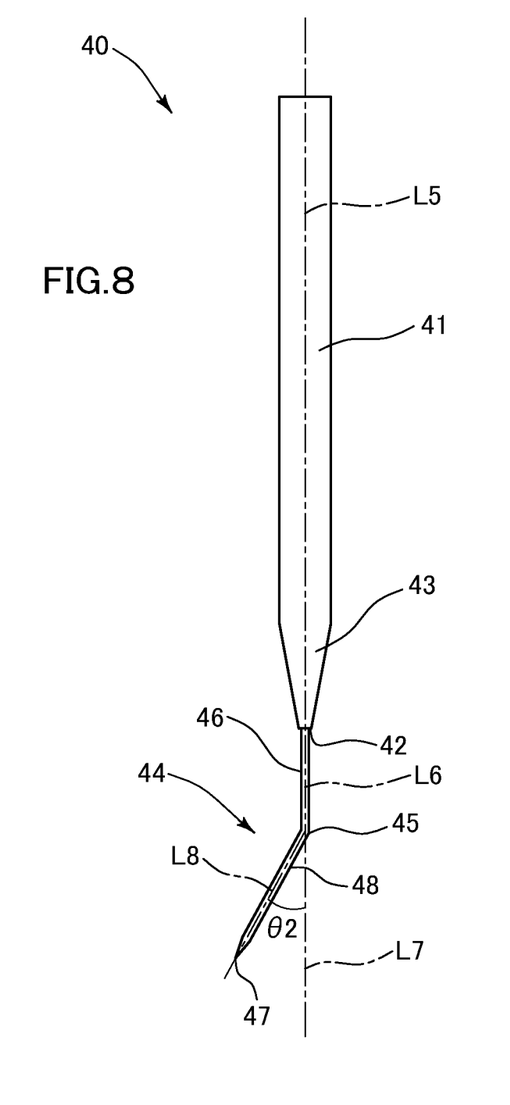
FIG. 8 is a side view of an ophthalmic instrument according to a second embodiment.

FIG. 8 illustrates an instrument 40 according to the second embodiment. Similar to the instrument 1 in FIG. 1, the instrument 40 is a tube member retaining instrument for retaining the tube member 10 (see FIG. 2) such that the tube member 10 is stuck into the cornea of an eye to be operated, during ophthalmic surgery.

The instrument 40 in FIG. 8 has a rod-shaped main body 41 and a needle portion 44. The main body 41 is made of, for example, resin, and has a shape in which the entirety thereof extends in a straight manner. That is, no bent portion is present in the main body 41. A portion 43, from a tip end 42, of the main body 41 may be formed, for example, in a shape in which the diameter thereof gradually decreases toward the tip end 42 (that is, in a tapered shape). The main body 41 serves as a grip portion (straight portion).

The needle portion 44 is made of metal and formed as a molded member separate from the main body 41. The needle portion 44 is connected to the tip end 42 of the main body 41. The needle portion 44 is formed in a shape in which the tip end side thereof is provided at an angle with respect to the base end side thereof. Specifically, in the middle of a portion projecting from the main body 41, the needle portion 44 has a bent portion 45 as a direction change portion that changes the direction in which the needle portion 44 extends, to another direction. The needle portion 44 has a single bent portion 45. A portion 46 of the needle portion 44 from the tip end 42 of the main body 41 to the bent portion 45 is referred to as a base end side portion, and the base end side portion 46 extends in a straight manner in the same direction as the direction in which the main body 41 extends. That is, a central axis L6 of the base end side portion 46 coincides with an extension line of a central axis L5 of the main body 41.

A portion 48 of the needle portion 44 from the bent portion 45 to a tip end 47 is referred to as a tip end side portion, and the tip end side portion 48 is formed in a straight shape but is provided at an angle θ2 with respect to the base end side portion 46. The angle θ2 is an angle formed between an extension line L7 of the central axis L6 of the base end side portion 46 (which is also the extension line of the central axis L5 of the main body 41) and a central axis L8 of the tip end side portion 48. The angle θ2 is set to an angle equal to the angle θ1 in FIG. 1. In addition, the length of the tip end side portion 48 is set to a length equal to the length a of the needle portion 6 in FIG. 1.

Figure 9:
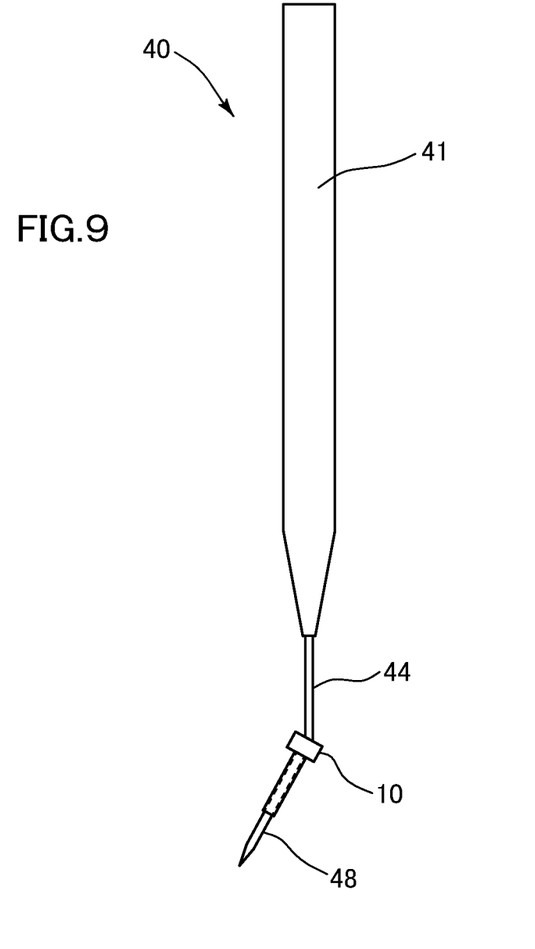
FIG. 9 is a diagram showing that a tube member is mounted on the ophthalmic instrument according to the second embodiment.

When retaining the tube member 10 in FIG. 2 at an eyeball, first, the tube member 10 is mounted onto the instrument 40 (tip end side portion 48) by inserting the tip end side portion 48 of the needle portion 44 through the tube member 10 as shown in FIG. 9. Thereafter, the operator holds the main body 41 and retains the tube member 10 at an outer peripheral portion of the cornea in the same manner as the procedure in FIG. 4 to FIG. 6.

In this embodiment, since the portion 48 (tip end side portion) from the tip end 47 of the needle portion 44 is provided at an angle with respect to the direction in which the main body 41 serving as a straight portion extends as described above, the same effects as those of the first embodiment can be achieved. In addition, in this embodiment, since the entirety of the main body 41 is formed in a straight shape, in other words, no bent portion is present in the main body 41, the configuration of the main body 41 can be simplified, and, for example, a conventional main body can be used.

Third Embodiment

Next, a third embodiment will be described focusing on the differences from the first and second embodiments. The tube member retaining instrument of the second embodiment is configured to have a bent portion in the middle of the needle portion. However, a tube member retaining instrument of the third embodiment is configured such that the entirety of the portion, of the needle portion, projecting from the main body is provided at an angle with respect to the main body.

Figure 10:
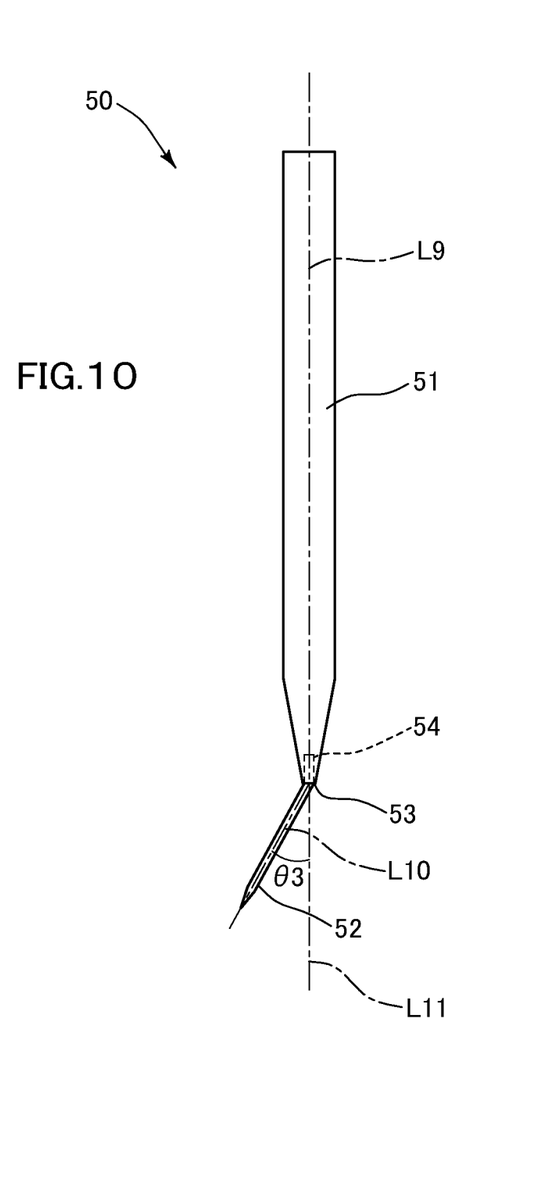
FIG. 10 is a side view of an ophthalmic instrument according to a third embodiment.

FIG. 10 illustrates an instrument 50 according to the third embodiment. Similar to the instrument 1 in FIG. 1, the instrument 50 is a tube member retaining instrument for retaining the tube member 10 (see FIG. 2) such that the tube member 10 is stuck into the cornea of an eye to be operated, during ophthalmic surgery.

The instrument 50 in FIG. 10 has a rod-shaped main body 51 and a needle portion 52. The main body 51 serves as a grip portion (straight portion) and is formed in a shape that is the same as that of the main body 41 in FIG. 8.

The needle portion 52 is made of metal and formed as a molded member separate from the main body 51. The needle portion 52 is connected to a tip end 53 of the main body 51. The entirety of a portion, of the needle portion 52, projecting from the main body 51 is formed in a straight shape, and no bent portion is present in this projecting portion. The length of the portion, of the needle portion 52, projecting from the main body 51 is set to a length equal to the length a of the needle portion 6 in FIG. 1.

The needle portion 52 is connected to the main body 51, for example, by embedding a base end side portion 54 thereof in the main body 51. In this case, the needle portion 52 is bent at the position of the tip end 53 of the main body 51, and the tip end side from the bent portion thereof projects from the main body 51.

An angle θ3 formed between a central axis L10 of the needle portion 52 and an extension line L11 of a central axis L9 of the main body 51 is set to an angle equal to the angle θ1 in FIG. 1.

When retaining the tube member 10 in FIG. 2 at an eyeball using the instrument 50, first, the tube member 10 is mounted onto the instrument 50 by inserting the needle portion 52 through the tube member 10. Thereafter, the operator holds the main body 51 and retains the tube member 10 at an outer peripheral portion of the cornea in the same manner as the procedure in FIG. 4 to FIG. 6.

In this embodiment, the same effects as those of the first and second embodiments are achieved, and the length of the needle portion 52 can be inhibited from being larger than necessary, since the entirety of the portion of, the needle portion 52, projecting from the main body 51 is formed in a straight shape and no bent portion is present therein as described above.

This disclosure is not limited to the above embodiments, and various modifications may be made. For example, although the case of retaining the tube member such that the tube member is stuck into the cornea has been described in the above embodiments, the instrument of this disclosure may be applied to an instrument for retaining a tube member such that the tube member is stuck into a sclera. In this case, the tube member is retained at an eyeball, for example, in order to introduce a liquid, a surgical instrument, or light into the vitreous body inside the sclera.

For surgery other than glaucoma surgery (for example, cataract surgery), the tube member may be retained at an eyeball.

Although the example in which the main body including a straight portion (grip portion) and the needle portion are formed as molded members separate from each other has been described in the above embodiments, the main body and the needle portion may be formed as an integrally molded member made of the same material.

Although the needle portion has a shape in which the direction thereof is suddenly changed in the middle of the needle portion in the above second embodiment, the needle portion may have a shape in which the direction thereof is gradually changed (that is, a shape in which the bent portion is curved).

DESCRIPTION OF THE REFERENCE CHARACTERS 1, 40, 50 tube member retaining instrument (ophthalmic instrument)
2 main body
41, 51 main body (straight portion)
3 straight portion
4 bent portion of main body
6, 44, 52 needle portion
10 tube member
21 cornea
45 bent portion of needle portion

What is claimed is:

1. An ophthalmic instrument for an ophthalmic surgery, comprising:
   a needle portion for penetrating into an eyeball for creating a hole;
   a main body having at least a straight portion extending along a central axis and a bent portion being tapered and connected to the straight portion at a predetermined angle with the central axis at one end of the bent portion and also connected to the needle portion at the other end of the bent portion;
   a tube member releasably engaged on the needle portion before penetration into an eyeball and for providing communication during ophthalmic surgery between an inside and an outside of the eyeball after the penetration to be independently left in an outer membrane of the eyeball;
   the needle portion further comprising a portion that is embedded in the bent portion; and
   wherein the needle portion is made of a material that is different from a material of the main body.

2. The ophthalmic instrument for an ophthalmic surgery according to claim 1, the main body further comprising an anti-slippery portion on the main body.

* * * * *